US00PP23055P2

(12) United States Plant Patent
Goto et al.

(10) Patent No.: US PP23,055 P2
(45) Date of Patent: Sep. 18, 2012

(54) ***PETUNIA* PLANT NAMED 'HOOBENIHIME'**

(50) Latin Name: *Petunia hybrida*
Varietal Denomination: Hoobenihime

(75) Inventors: Koji Goto, Fujisawa (JP); Fusako Goto, Koza (JP); Susumu Goto, Koza (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 13/199,130

(22) Filed: Aug. 19, 2011

(51) Int. Cl.
*A01H 5/00* (2006.01)

(52) U.S. Cl. ..... Plt./356.13

(58) Field of Classification Search ..... Plt./356.13
See application file for complete search history.

*Primary Examiner* — June Hwu
*Assistant Examiner* — Louanne Krawczewicz Myers
(74) *Attorney, Agent, or Firm* — Jondle & Associates, P.C.

(57) ABSTRACT

A *Petunia* variety named 'Hoobenihime' particularly distinguished by having red-purple flowers with a dark purple edge and small flower size is disclosed.

1 Drawing Sheet

Genus and species: *Petunia hybrida.*
Variety denomination: 'Hoobenihime'.

BACKGROUND OF THE NEW PLANT

The present invention comprises of a new and distinct cultivar of *Petunia*, botanically known as *Petunia hybrida*, and hereinafter referred to by the cultivar name 'Hoobenihime'. It is characterized by having a purple flower with a dark purple edge and a small flower size. *Petunia* variety 'Hoobenihime' originated from a single plant mutation in Kanagawa, Japan in 2007. The parent was a proprietary *Petunia* breeding line named 'Usubenihime' having a pink flower with a dark pink edge and a small flower size.

In December 2006, the original breeding line 'Usubenihime' was vegetatively propagated from plant cuttings. In May 2007, a single plant mutation which had darker colored flowers was discovered in the trial. In November 2007, the selection was vegetatively propagated in Salinas, Calif. from cuttings of the plant mutation. In May 2008, plants of the selection were cultivated and the resulting plants showed the same flower characteristics as the single plant mutation. Plants of the selection were trialed again continuously to check for uniformity.

In April 2009, the selected line was observed to have its distinct characteristics remain uniform and stable. The selected plant line was confirmed to reproduce true to type in successive generations of asexual propagation. The selection was subsequently named 'Hoobenihime'.

Plant Variety Protection for this variety was applied for in Japan on Aug. 24, 2010. 'Hoobenihime' has not been made publicly available more than one year prior to filing of this application

DESCRIPTION OF THE PHOTOGRAPHS

This new *Petunia* plant is illustrated by the accompanying photographs which show the plant form, foliage, and flowers. The colors shown are as true as can be reasonably obtained by conventional photographic procedures.

Figure 1:
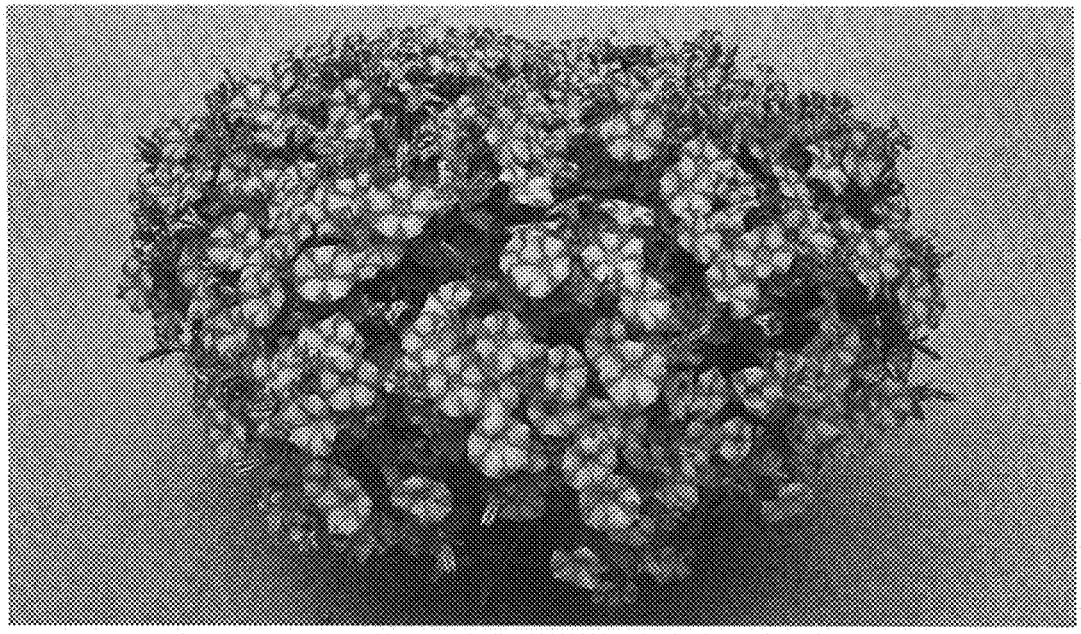
Figure 2:
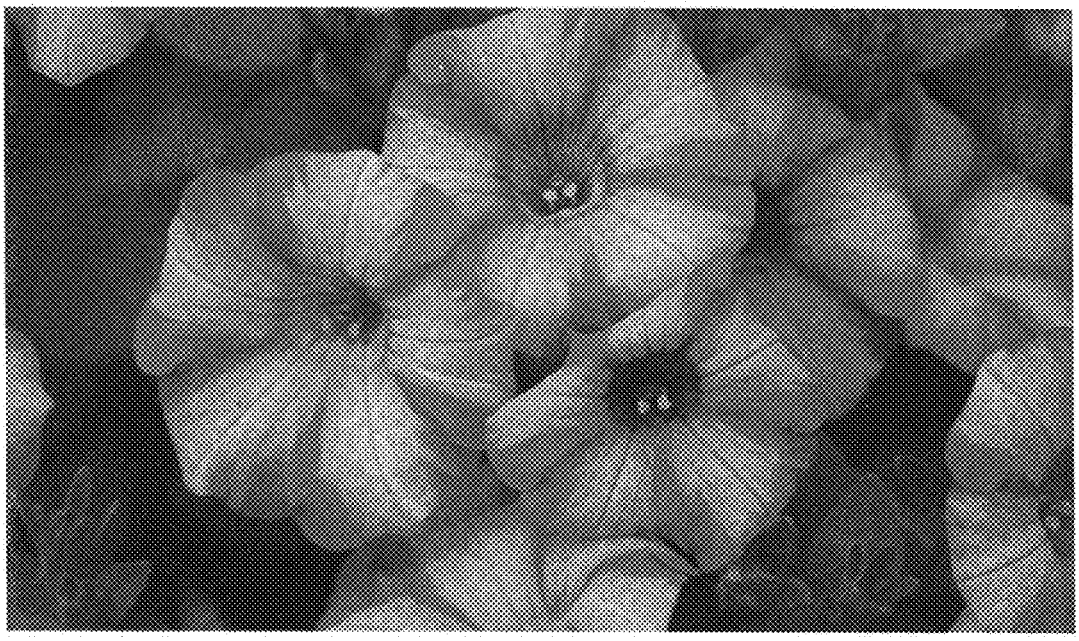

FIG. 1 shows the overall plant habit.
FIG. 2 shows the mature inflorescence.

DESCRIPTION OF THE NEW VARIETY

Data was obtained from plants grown 5 months from transplant to 8-inch pots from rooted cuttings in Salinas, Calif., under greenhouse conditions. Plants were pinched once during growth.

The following traits and characteristics describe the new variety. Color references are to The Royal Horticultural Society Colour Chart, 4th edition. Anatomic labels are from *The Cambridge Illustrated Glossary of Botanical Terms*, by M. Hickey and C. King, Cambridge University Press.

DETAILED BOTANICAL DESCRIPTION

Classification:
- *Family.*—Solanaceae.
- *Species.*—*Petunia hybrida.*
- *Common name.*—*Petunia.*

Parentage:
- *Parent.*—Proprietary *Petunia* variety named 'Usubenihime'.

Plant description:
- *Life cycle.*—Annual/tender perennial in warm climates.
- *Habit.*—Freely branching.
- *Height.*—Approximately 19.0 cm to 20.0 cm from soil line to top of foliage.
- *Spread.*—Approximately 55.0 cm to 56.0 cm.
- *Form.*—Decumbent (trailing).

Propagation:
- *Type cuttings.*—Vegetative.
- *Time to produce a rooted cutting.*—Approximately 4 weeks.
- *Time to bloom from propagation.*—Approximately 6 to 8 weeks.

Environmental conditions for plant growth: The terminal 1.0 to 1.5 inches of an actively growing stem was excised. The vegetative cuttings were propagated in five to six weeks. The base of the cuttings were dipped for 1 to 2 seconds in a 1:9 solution of Dip 'N Grow (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Stems:
- *Color*.—RHS 143B (Green).
- *Diameter*.—Approximately 2.0 mm.
- *Length*.—Approximately 10.0 cm to 12.0 cm.
- *Description*.—Pliable; circular cross-section.
- *Pubescence*.—Heavy.
- *Pubescence color*.—RHS N155A (White).

Lateral branches:
- *Number*.—Approximately 8 main basal branches; many secondary and tertiary branches.
- *Length*.—30.0 cm to 32.0 cm.
- *Diameter*.—4.0 mm.
- *Internode length*.—Approximately 2.5 cm.
- *Color*.—RHS 143B (Green).
- *Texture*.—Dull.

Leaves:
- *Arrangement*.—Alternate.
- *Shape*.—Ovate.
- *Apex*.—Obtuse.
- *Base*.—Attenuate.
- *Margin*.—Entire.
- *Attachment*.—Petiolate.
- *Surface texture* (*both surfaces*).—Dull, waxy and sticky.
- *Surface pubescence*.—Slight.
- *Pubescence color*.—RHS N155A (White).
- *Variegation*.—Absent.
- *Fragrance*.—Absent.
- *Venation*.—Pinnate. Upper surface vein color: RHS 144A (Yellow-green). Lower surface vein color: RHS 144B (Yellow-green).
- *Length*.—3.0 cm.
- *Width*.—2.0 cm.
- *Color*.—Upper surface: RHS 137A (Green). Lower surface: RHS 137C (Green).
- *Petiole*.—Length: Approximately 5.0 mm. Color: RHS 143C (Green). Diameter: 1.0 mm. Texture: Heavy pubescence. Pubescence color: RHS N155A (White).

Inflorescence:
- *Number of flowers per node*.—1.
- *Diameter*.—4.0 cm.
- *Flower type*.—Solitary.
- *Flowering requirements*.—Will flower so long as temperature is above 13° C. and greater than 12 hours of daylight.
- *Fragrance*.—Absent.
- *Flowering season*.—Spring through fall.
- *Lastingness of flowers*.—2 to 3 weeks.

Bud description:
- *Color*.—RHS 83B (Violet).
- *Length*.—3.0 cm.
- *Diameter*.—7.0 mm.
- *Shape*.—Cylindrical.
- *Surface*.—Dull and sticky.
- *Pubescence*.—Moderate.
- *Pubescence color*.—RHS N155A (White).

Corolla:
- *Shape*.—Funnel-shaped with 5 fused petals.
- *Depth*.—0.5 cm.
- *Diameter*.—4.0 cm.
- *Tube length*.—2.0 cm.
- *Tube diameter*.—1.0 cm
- *Tube pubescence* (*inner and outer surfaces*).—Heavy.
- *Tube pubescence color* (*inner and outer surfaces*).—RHS N155A (White).
- *Tube color*.—Inner: Closest to RHS 85A (Violet) with small veins of RHS 83A (Violet). Outer: Closest to RHS 85C (Violet) with small veins of RHS 83A (Violet) and large veins of RHS 144A (Yellow-green).

Petals:
- *Shape*.—Obcordate.
- *Length*.—2.0 cm.
- *Width*.—1.5 cm.
- *Apex*.—Acuminate.
- *Margin*.—Entire.
- *Pubescence* (*both surfaces*).—Glabrous.
- *Color*.—Upper surface: Closest to RHS N74C (Red-purple) with RHS N74A (Red-purple) at edge. Lower surface: Closest to RHS N74D (Red-purple) with RHS N74B (Red-purple) at edge and RHS 144A (Yellow-green) at mid-vein Venation (upper surface): RHS N74A (Red-purple).

Calyx description:
- *Arrangement*.—5 sepals; free.
- *Sepal shape*.—Lanceolate.
- *Sepal length*.—1.5 cm.
- *Sepal width*.—3.0 mm.
- *Sepal apex*.—Obtuse.
- *Sepal base*.—Attenuate.
- *Sepal margin*.—Entire.
- *Sepal attachment*.—Sessile.
- *Sepal color*.—Upper surface: RHS 137A (Green). Lower surface: RHS 137C (Green).
- *Sepal texture* (*both surfaces*).—Dull, waxy and sticky with slight pubescence.
- *Sepal pubescence color* (*both surfaces*).—RHS N155A (White).

Peduncle description:
- *Length*.—3.0 cm.
- *Diameter*.—1.0 mm.
- *Color*.—RHS 143A (Green).
- *Texture*.—Heavy pubescence.
- *Pubescence color*.—RHS N155A (White).

Reproductive organs:
- *Stamen*.—Stamen number: 5, free. Stamen form: Arranged adjacent to pistil. Filament color: RHS 145D (Yellow-green). Anther color: Closest to RHS 85A (Violet). Pollen description: Powdery and abundant. Pollen color: RHS 85D (Violet).
- *Pistil*.—Pistil number: 1. Pistil length: 1.8 cm. Stigma color: Slightly darker than RHS 85A (Violet). Stigma length: 2.0 mm. Style length: 1.6 cm. Style color: RHS 145D (Yellow-green).
- *Ovary arrangement*.—Superior.
- *Ovary surface color*.—RHS 144C (Yellow-green).
- *Seed production*.—None observed.

Disease and insect resistance: No particular resistance or susceptibility observed.

Temperature tolerance: No particular temperature tolerances observed.

COMPARISON WITH KNOWN VARIETIES

'Hoobenihime' is a new and distinct cultivar of *Petunia* owning to its purple flower with a dark purple edge and small flower size. 'Hoobenihime' is most similar to the commercial *Petunia* variety 'Temari', U.S. Plant Pat. No. 16,588; however, there are differences as listed in the table below:

TABLE 1

| Characteristic | 'Hoobenihime' | 'Temari' |
|---|---|---|
| Petal color, upper surface | Closest to RHS N74C (Red-purple) with RHS 74A (Red-purple) edge | RHS 67C (Red-purple) with RHS 74A (Red-purple) edge |
| Petal color, lower surface | Closest to RHS N74D (Red-purple) with RHS N74B (Red-purple) at edge and RHS 144A (Yellow-green) at mid-vein | RHS 186D (Grayed-purple) with RHS 155A (White) |
| Flower diameter | 4.0 cm | 5.6 cm |

'Hoobenihime' is compared with its parental line in Table 2:

TABLE 2

| Characteristic | 'Hoobenihime' | Parent: 'Usubenihime' |
|---|---|---|
| Flower color | Red-purple flower with a dark purple edge | pink flower with a dark pink edge |

We claim:

1. A new and distinct variety of *Petunia* plant named 'Hoobenihime' as shown and described herein.

* * * * *